United States Patent [19]

Fuchs et al.

[11] Patent Number: 5,502,185

[45] Date of Patent: Mar. 26, 1996

[54] PREPARATION OF LACTAMS

[75] Inventors: Eberhard Fuchs, Frankenthal; Tom Witzel, Ludwigshafen, both of Germany

[73] Assignee: BASF Aktiengesellschaft, Ludwigshafen, Germany

[21] Appl. No.: 358,413

[22] Filed: Dec. 19, 1994

[30] Foreign Application Priority Data

Jun. 28, 1994 [DE]  Germany ............... 44 22 610.1

[51] Int. Cl.⁶ .................... C07D 201/08
[52] U.S. Cl. ............ 540/538; 540/451; 546/243; 548/554
[58] Field of Search ................ 540/451, 538; 546/243; 548/554

[56] References Cited

U.S. PATENT DOCUMENTS

| | | | |
|---|---|---|---|
| 2,301,964 | 11/1942 | Martin | 540/538 |
| 2,357,484 | 9/1944 | Martin | 540/538 |
| 2,956,051 | 10/1960 | Duxbury et al. | 540/538 |
| 3,658,810 | 4/1972 | Tanaka et al. | 540/538 |
| 4,599,199 | 7/1986 | Fuchs | 540/538 |
| 4,767,857 | 8/1988 | Merger et al. | 540/538 |
| 4,963,673 | 10/1989 | Merger et al. | 540/538 |

*Primary Examiner*—Robert T. Bond
*Attorney, Agent, or Firm*—Keil & Weinkauf

[57] ABSTRACT

Cyclic lactams are prepared by reacting an aminocarboxylic acid compound of the formula I $$H_2N—(CH_2)_m—COR^1 \qquad I$$

where $R^1$ is —OH, —O—$C_1$–$C_{12}$-alkyl or —$NR^2R^3$ and $R^2$ and $R^3$, independently of one another, are each hydrogen, $C_1$–$C_{12}$-alkyl or $C_5$–$C_8$-cycloalkyl and m is an integer from 3 to 12, with water by a process in which the reaction is carried out in the liquid phase using a heterogeneous catalyst.

5 Claims, No Drawings

PREPARATION OF LACTAMS

The present invention relates to a process for the preparation of cyclic lactams by reacting an aminocarboxylic acid compound of the formula I $$H_2N\text{---}(CH_2)_m\text{---}COR^1 \qquad I$$

where $R^1$ is —OH, —O—$C_1$–$C_{12}$-alkyl or -$NR^2R^3$ and $R^2$ and $R^3$, independently of one another, are each hydrogen, $C_1$–$C_{12}$-alkyl or $C_5$–$C_8$-cycloalkyl and m is an integer from 3 to 12, with water.

U.S. Pat. No. 3,485,821 relates to the uncatalyzed conversion of aminocaproic acid, aminocaproamide and alkyl-substituted derivatives thereof into caprolactam or alkyl-substituted caprolactam by carrying out the reaction in water at from 150° to 350° C., it being possible to add ammonium salts to the water. However, the conversions to caprolactam are not higher than 90%.

DE-A 2,535,689 describes a process for the preparation of caprolactam by converting 6-aminocaproic acid dissolved in methanol or ethanol, the solvent having an alcohol content of at least 60% by volume and the reaction being carried out at from 170° to 200° C. According to DE-A 2,535,689, higher temperatures, in particular 220° C. or higher, lead to the increased formation of the corresponding alkyl ester of 6-aminocaproic acid, which finally results in increased oligomer formation. According to this document, water contents above 40% by volume should lead to the formation of open-chain polyamides. For commercial use, the addition of the 6-aminocaproic acid is a considerable disadvantage since the aminocaproic acid should be completely dissolved before it is converted into caprolactam, and hence 6-aminocaproic acid must be constantly added and its consumption monitored.

Ind. Eng. Chem. Process Des. Dev. 17(1) (1978), 9–16 (Mares et al.) describes the conversion of 6-aminocaproic acid, both in water and in ethanol, into caprolactam without the addition of a catalyst. The yield of caprolactam in water at a reaction temperature of 211° C. is only 65%, while yields of up to 98% are said to be achievable in pure ethanol. However, the yields of 92% or higher described by Mares et al. could not be repeated in our own experiments. Rather, these high yields can be explained only by the fact that Mares et al. did not use a 10% strength by weight solution of 6-aminocaproic acid but cyclized minimum 6-aminocaproic acid concentrations to give caprolactam by continuous addition of 6-aminocaproic acid to the ethanolic solution. Since caprolactam is stable under the chosen reaction conditions, it was possible to obtain the high yields (92% and 98%) only by virtue of the fact that the concentration of caprolactam increased during the reaction. This assumption is supported by U.S. Pat. No. 2,535,689 (with Mares as coinventor). Example 1 of this U.S. patent indicates that a reaction of the 6-aminocaproic acid is to be prevented before the 6-aminocaproic acid has completely dissolved. For this purpose, the 6-aminocaproic acid should be added so slowly that no solid acid is present in the solvent but the 6-aminocaproic acid is dispersed virtually immediately in the hot solvent and is completely dissolved or is dispersed during heating. Since the maximum solubility of 6-aminocaproic acid in both cold and boiling ethanol (78° C.) is only 1.3 g/l (=0.13% by weight), it is clear that, in Mares et al., 6-aminocaproic acid could be added only gradually in order to obtain a solution which, purely theoretically, contained 10% by weight of 6-aminocaproic acid. Otherwise, the technical procedure for such metering at 200° C. and 80 bar entails very great difficulties as well as a long time.

In Mares et al. (Ind. Eng. Chem. Process Des. Dev. 17(1) (1978), 9–16), the conversion of ethyl 6-aminocaproate in ethanol into caprolactam is also investigated. It is found that quantitative cyclization is possible only at low temperatures and at high dilution. According to Mares et al., in particular a caprolactam yield of only 90% is achievable from ethyl 6-aminocaproate at 200° C. and in a reaction time of 10 hours. According to Mares et al., the yield can be increased to not more than 95% at 150° C., but reaction times of 10 hours or more are out of the question for commercial use.

Mares et al. likewise describe the conversion of ethyl 6-aminocaproate in water into caprolactam at 200° C. and in a reaction time of five hours with a yield of not more than 62.5%. In the same publication, the conversion of 6-aminocaproamide into caprolactam, both in water and in ethanol, is investigated, and yields of not more than 71% in a reaction time of more than 70 minutes can be obtained.

Tetrahedron Lett. 21 (1980), 2443 describes the cyclization of 6-aminocaproic acid as a suspension in toluene in the presence of alumina or silica gel with removal of the water of reaction. For complete desorption of the caprolactam, the catalyst must be washed with methylene chloride/methanol and polymers must be precipitated with diethyl ether. The yield of caprolactam is 82% over alumina and 75% over silica gel, but the reaction time is 20 hours in each case.

EP-A 271 815 describes the cyclization of 6-aminocaproates to give caprolactam, the esters being dissolved in an aromatic hydrocarbon and then cyclized at from 100° to 320° C. with simultaneous removal of the alcohol formed.

Disadvantages are the separation of the alcohol under superatmospheric pressure as well as the aromatic hydrocarbons, which are expensive to remove since they are high-boiling, and the long reaction times, for example 14 hours when the reaction is carried out in o-xylene (140° C.).

EP-A 376 122 describes the cyclization of 6-aminocaproates in the presence of an aromatic hydrocarbon and water at from 230° to 350° C. to give caprolactam.

It is an object of the present invention to provide a process for the preparation of cyclic lactams by reacting an aminocarboxylic acid compound of the formula I $$H_2N\text{---}(CH_2)_m\text{---}COR^1 \qquad I$$

where $R^1$ is —OH, —O—$C_1$–$C_{12}$-alkyl or —$NR^2R^3$ and $R^2$ and $R^3$, independently of one another, are each hydrogen, $C_1$–$C_{12}$-alkyl or $C_5$–$C_8$-cycloalkyl and m is an integer from 3 to 12, with water, which process does not have the disadvantages described above.

We have found that this object is achieved by an improved process for the preparation of cyclic lactams by reacting an aminocarboxylic acid compound of the formula I $$H_2N\text{---}(CH_2)_m\text{---}COR^1 \qquad I$$

where $R^1$ is —OH, —O—$C_1$–$C_{12}$-alkyl or —$NR^2R^3$ and $R^2$ and $R^3$, independently of one another, are each hydrogen, $C_1$–$C_{12}$-alkyl or $C_5$–$C_8$-cycloalkyl and m is an integer from 3 to 12, with water by carrying out the reaction in the liquid phase using a heterogeneous catalyst.

The starting materials used in the novel process are aminocarboxylic acid compounds, preferably those of the formula I $$H_2N\text{---}(CH_2)_m\text{---}COR^1 \qquad I$$

where $R^1$ is —OH, —O—$C_1$–$C_{12}$-alkyl or -$NR^2R^3$ and $R^2$ and $R^3$, independently of one another, are each hydrogen, $C_1$–$C_{12}$-alkyl or $C_5$–$C_8$-cycloalkyl and m is 3, 4, 5, 6, 7, 8, 9, 10, 11 or 12.

If the preferred starting compounds are those in which $R^1$ is OH or —O—$C_1$-$C_4$-alkyl, such as —O-methyl, —O-ethyl, —O—n-propyl, —O-isopropyl, —O—n-butyl, —O—sec-butyl, —O—tert-butyl or —O—isobutyl, —$NR^2R^3$ is —$NH_2$, —NHMe, —NHEt, —$NMe_2$ or —$NEt_2$ and m is 5.

6-Aminocaproic acid, methyl 6-aminocaproate, ethyl 6-aminocaproate, 6-amino-N-methylcaproamide, 6-amino-N,N-dimethylcaproamide, 6-amino-N-ethylcaproamide, 6-amino-N,N-diethylcaproamide and 6-aminocaproamide are very particularly preferred.

The starting compounds are commercially available or can be prepared, for example, according to EP 234,295 and Ind. Eng. Chem. Process Des. Dev. 17 (1978), 9–16.

In the novel process, the aminocarboxylic acid compounds described above are reacted with water in the liquid phase using a heterogeneous catalyst to give cyclic lactams. When aminocarboxylic acid compounds of the general formula I are used, the corresponding cyclic lactams of the formula II

 II where m has the abovementioned meanings, are obtained. Particularly preferred lactams are those in which m is 4, 5 or 6, in particular 5 (in the latter case, caprolactam is obtained). The reaction is carried out in the liquid phase at in general from 140° to 320° C., preferably from 160° to 300° C.; the pressure is usually chosen to be from 0.5 to 25 MPa, but so that the reaction mixture is liquid under the conditions used. The residence times are as a rule from 5 to 120, preferably from 10 to 60, minutes.

Advantageously, the aminocarboxylic acid compound is used in the form of a 1–50, preferably 5–50, particularly preferably 5–25%, strength by weight solution in water or in a water/solvent mixture. Examples of solvents are alkanols, in particular $C_1$-$C_4$-alkanols, such as methanol, ethanol, n-propanol, isopropanol, n-butanol, isobutanol, sec-butanol and tert-butanol, polyols, such as diethylene glycol and tetraethylene glycol, lactams, such as pyrrolidone, caprolactam and alkyl-substituted lactams, in particular N-$C_1$-$C_4$-alkyllactams, such as such as [sic] N-methylpyrrolidone, N-methylcaprolactam or N-ethylcaprolactam. Ammonia, too, may be present in the reaction. Mixtures of organic solvents may of course also be used.

Heterogeneous catalysts which may be used are, for example: acidic, basic or amphoteric oxides of the elements of the second, third or fourth main group of the Periodic Table, such as boron oxide, alumina or silica as silica gel, kieselguhr, quartz or mixtures thereof, and oxides of metals of the second to sixth subgroups of the Periodic Table, such as titanium dioxide as anatase or rutile, zirconium oxide or mixtures thereof. Oxides of the lanthanides or actinides, such as lanthanum oxide, cerium oxide, thorium oxide, praseodymiumoxide or neodymium oxide, or mixtures thereof with abovementioned oxides may also be used. Further catalysts may be, for example: vanadium oxide, niobium oxide, iron oxide, chromium oxide, molybdenum oxide, tungsten oxide and mixtures thereof. Mixtures of these oxides with one another are also possible.

The abovementioned oxides may be doped with compounds of main groups I and VII of the Periodic Table or may contain these.

Zeolites, phosphates and heteropoly acids and acidic and alkaline ion exchangers, for example Naphion®, are also examples of suitable catalysts.

If required, these catalysts may contain up to 50% by weight in each case of copper, tin, zinc, manganese, iron, cobalt, nickel, ruthenium, palladium, platinum, silver or rhodium.

The amount of catalyst depends as a rule on the procedure: in a batchwise procedure, the amount of catalyst is chosen to be from 0.1 to 50, preferably from 1 to 30, % by weight, based on the aminocarboxylic acid compound of the general formula I; in the continuous procedure, the catalyst space velocity is chosen to be from 0.1 to 5 kg per l per h, based on the aminocarboxylic acid compound of the general formula I.

In the novel process, cyclic lactams, in particular caprolactam, are obtained in high yield.

EXAMPLES

Example 1

A solution of 6-aminocaproic acid in water was passed, at 100 bar, into a heated tube reactor which had a capacity of 100 ml, diameter of 9 mm and a length of 400 mm and was filled with titanium dioxide (anatase) in the form of 1.5 mm extrudates. The product stream leaving the reactor was analyzed by gas chromatography and high-pressure liquid chromatography (HPLC).

| Aminocarboxylic acid [%] | Water [%] | Temperature [°C.] | Residence time [min] | Yield [%] |
|---|---|---|---|---|
| 10 | 90 | 220 | 15 | 66 |
| 10 | 90 | 220 | 30 | 76 |

Example 2

Similarly to the experiments described in Example 1, a solution of aminocaproic acid in ethanol/water was pumped through a tube reactor filled with titanium oxide extrudates.

| Aminocarboxylic acid [%] | Water [%] | Ethanol [°C. [sic]] | Temperature [°C.] | Residence time [min] | Yield [%] |
|---|---|---|---|---|---|
| 10 | 40 | 50 | 220 | 15 | 98 |
| 10 | 40 | 50 | 220 | 30 | 90 |

Example 3

Similarly to the experiments described in Example 1, a solution of ethyl aminocaproate in ethanol, in the presence of water, was pumped through a tube reactor filled with titanium oxide extrudates.

| Ethyl aminocaproate [%] | Water [%] | Ethanol [°C. [sic]] | Temperature [°C.] | Residence time [min] | Conversion [%] | Selectivity [%] | Yield [%] |
|---|---|---|---|---|---|---|---|
| 10 | 1.1 | 88.9 | 220 | 15 | 97 | 93 | 90 |
| 10 | 1.1 | 88.9 | 220 | 30 | 97 | 85 | 83 |
| 10 | 1.1 | 88.9 | 220 | 60 | 100 | 79 | 79 |
| 10 | 4.4 | 85.6 | 220 | 30 | 97 | 95 | 92 |

Comparative Example

In each case a 10% strength by weight solution of 6-aminocaproic acid in ethanol was heated to 200° C. during different residence times, according to Ind. Eng. Chem. Process Des. Dev. 17 (1978), 16. The results are listed in the table below.

| Residence time [min] | Temperature [°C.] | Conversion [%] | Selectivity [%] | Yield of caprolactam [%] |
|---|---|---|---|---|
| 10 | 200 | 90 | 80 | 72 |
| 15 | 200 | 87 | 93 | 80 |
| 20 | 200 | 90 | 90 | 81 |
| 30 | 200 | 90 | 91 | 82 |
| 40 | 200 | 91 | 88 | 80 |

Yields above 82% were not obtained.

We claim:

1. A process for the preparation of a cyclic lactam by reacting an aminocarboxylic acid compound of the formula I $$H_2N-(CH_2)_m-COR^1 \qquad I$$

where $R^1$ is —OH, —o—$C_1$–$C_{12}$-alkyl or —$NR^2R^3$ and $R^2$ and $R^3$, independently of one another, are each hydrogen, $C_1$–$C_{12}$-alkyl or $C_5$–$C_8$-cycloalkyl and m is an integer from 3 to 12, with water, wherein the reaction is carried out in the liquid phase using a heterogeneous catalyst.

2. A process as defined in claim 1, wherein the reaction is carried out at from 140° to 320° C.

3. A process as defined in claim 1, wherein the aminocarboxylic acid compound used is a compound selected from the group consisting of 6-aminocaproic acid, methyl 6-aminocaproate, ethyl 6-aminocaproate, 6-amino-N-methylcaproamide, 6-amino-N,N-dimethylcaproamide, 6-amino-N-ethylcaproamide, 6-amino-N,N-diethylcaproamide and 6-aminocaproamide.

4. A process as defined in claim 1, wherein the reaction is carried out in water or in a mixture of water and an organic solvent.

5. A process as defined in claim 1, wherein the reaction is carried out at from 140° to 320° C., wherein the aminocarboxylic acid compound is selected from the group consisting of 6-aminocaproic acid, methyl 6-aminocaproate, ethyl 6-aminocaproate, 6-amino-N-methylcaproamide, 6-amino-N,N-dimethylcaproamide, 6-amino-N-ethylcaproamide, 6-amino-N,N-diethylcaproamide and 6-aminocaproamide, and wherein the reaction is carried out in water or a mixture of water and an organic solvent.

* * * * *

UNITED STATES PATENT AND TRADEMARK OFFICE
CERTIFICATE OF CORRECTION

PATENT NO. : 5,502,185
DATED : March 26, 1996
INVENTOR(S) : Fuchs, et al.

It is certified that error appears in the above-indentified patent and that said Letters Patent is hereby corrected as shown below:

Column 5, claim 1, line 36, "-o-$C_1$-$C_{12}$-alkyl" should read -- -O-$C_1$-$C_{12}$-alkyl --.

Signed and Sealed this

Thirteenth Day of August, 1996

Attest:

BRUCE LEHMAN

*Attesting Officer*     *Commissioner of Patents and Trademarks*